(12) United States Patent
Stumpp

(10) Patent No.: US 9,579,451 B2
(45) Date of Patent: Feb. 28, 2017

(54) DEVICE FOR ADMINISTERING A CANNULA

(75) Inventor: Uwe Stumpp, Frittlingen (DE)

(73) Assignees: Uwe STUMPP, Frittlingen (DE); Christian MANTSCH, Minden (DE)

( * ) Notice: Subject to any disclaimer, the term of this patent is extended or adjusted under 35 U.S.C. 154(b) by 830 days.

(21) Appl. No.: 12/672,510

(22) PCT Filed: Jul. 28, 2008

(86) PCT No.: PCT/EP2008/006211
§ 371 (c)(1),
(2), (4) Date: Feb. 6, 2010

(87) PCT Pub. No.: WO2009/018937
PCT Pub. Date: Feb. 12, 2009

(65) Prior Publication Data
US 2012/0004612 A1 Jan. 5, 2012

(30) Foreign Application Priority Data

Aug. 9, 2007 (DE) .................... 20 2007 011 154 U

(51) Int. Cl.
*A61M 5/158* (2006.01)
*A61M 5/32* (2006.01)
*A61M 39/02* (2006.01)

(52) U.S. Cl.
CPC ........... *A61M 5/158* (2013.01); *A61M 5/3257* (2013.01); *A61M 39/0208* (2013.01);
(Continued)

(58) Field of Classification Search
CPC ................ A61M 5/3273; A61M 5/158; A61M 25/0618; A61M 25/0606; A61M 2005/325;
(Continued)

(56) References Cited

U.S. PATENT DOCUMENTS 5,147,303 A * 9/1992 Martin .......................... 604/110
5,246,427 A 9/1993 Sturman et al.
(Continued)

FOREIGN PATENT DOCUMENTS

DE 19745654 A1 4/1999
DE 10333118 A1 6/2004
(Continued)

OTHER PUBLICATIONS

Specialized Health Products, Inc., SHPI is proud to bring you the Liftloc® Safety Infusion Set, 2 pages, 2004.
MiniLoc™ Safety Infusion Set, 2 pages, 2005.

*Primary Examiner* — Justine Yu
*Assistant Examiner* — Shefali Patel
(74) *Attorney, Agent, or Firm* — Richard M. Goldberg

(57) ABSTRACT

A device for administering a cannula (14), having a basic element (10),the cannula (14), a tip (16) of which protrudes beyond the basic element (10) in a ready to use position of the device, a traction element (12), which is movable with respect to the basic element (10), and a releasable pretensioning device (36, 38, 40) for pretensioning the traction element (12) with respect to the basic element (10) in the ready to use position of the device, wherein the traction element (12) interacts with the cannula (14) so that, when the pretensioning device (36, 38, 40) of the traction element (12) is released, the tip (16) of the cannula (14) retracts into the basic element (10).

14 Claims, 5 Drawing Sheets

(52) U.S. Cl.
CPC .............. *A61M 2005/1581* (2013.01); *A61M 2005/1583* (2013.01); *A61M 2005/1585* (2013.01); *A61M 2005/325* (2013.01); *A61M 2005/3246* (2013.01)

(58) Field of Classification Search
CPC .. A61M 2005/1581; A61M 2005/1583; A61M 2005/1585; A61M 2005/3246; A61M 5/3257
USPC ..................... 604/164.08, 164.11, 164.12
See application file for complete search history.

(56) References Cited

U.S. PATENT DOCUMENTS

| | | | |
|---|---|---|---|
| 6,238,375 | B1 | 5/2001 | Powell |
| 6,500,155 | B2 | 12/2002 | Sasso |
| 6,613,015 | B2 | 9/2003 | Sandstrom et al. |
| 6,623,462 | B2 | 9/2003 | Guzzo et al. |
| 6,629,959 | B2 * | 10/2003 | Kuracina ............... A61B 5/154 604/192 |
| 6,676,633 | B2 | 1/2004 | Smith et al. |
| 6,719,721 | B1 | 4/2004 | Okazaki et al. |
| 6,755,805 | B1 | 6/2004 | Reid |
| 6,824,530 | B2 | 11/2004 | Wagner et al. |
| 6,918,894 | B2 | 7/2005 | Fleury et al. |
| 6,969,372 | B1 * | 11/2005 | Halseth .................. 604/164.08 |
| 6,997,902 | B2 | 2/2006 | Thorne et al. |
| 7,303,544 | B2 | 12/2007 | Bütikofer et al. |
| 7,347,842 | B2 | 3/2008 | Thorne et al. |
| 7,351,230 | B2 | 4/2008 | Smith et al. |
| 7,377,908 | B2 | 5/2008 | Buetikofer et al. |
| 2002/0173749 | A1 | 11/2002 | Wagner et al. |
| 2003/0069546 | A1 | 4/2003 | Sandstrom et al. |
| 2004/0138613 | A1 | 7/2004 | Reid |
| 2006/0015063 | A1 | 1/2006 | Bütikofer et al. |
| 2006/0030825 | A1 | 2/2006 | Enns et al. |
| 2006/0074387 | A1 | 4/2006 | Thorne et al. |
| 2006/0173414 | A1 | 8/2006 | Buetikofer et al. |
| 2007/0276320 | A1 | 11/2007 | Wall et al. |
| 2007/0293826 | A1 | 12/2007 | Wall et al. |

FOREIGN PATENT DOCUMENTS

| | | |
|---|---|---|
| EP | 0615768 B1 | 1/1994 |
| EP | 1256356 A2 | 11/2001 |
| EP | 1256355 B1 | 11/2002 |
| EP | 0777506 B1 | 12/2002 |
| EP | 1749547 A1 | 2/2007 |
| WO | 0241932 A2 | 5/2002 |
| WO | 03035143 A2 | 5/2003 |
| WO | 2004084970 A2 | 10/2004 |
| WO | 2005049109 A2 | 6/2005 |
| WO | 2005079441 A2 | 9/2005 |

\* cited by examiner

DEVICE FOR ADMINISTERING A CANNULA

CROSS-REFERENCE TO RELATED APPLICATION

The present application is the national stage entry of PCT/EP2008/006211, filed Jul. 28, 2008, which claims priority to German Patent Application No. 20 2007 011 154.1, filed Aug. 9, 2007.

BACKGROUND OF THE INVENTION

The invention relates to a device for administering a cannula.

In particular, the invention relates to a device for the percutaneous introduction of a cannula into an implanted port of a port catheter system. Such a port typically has a closing element, for example, of silicone, which is pierced by the cannula. The port catheter system may, for example, be a venous catheter for chemotherapy.

A device for administering a cannula is known, for which, after the port of a catheter is punctured with the cannula and after a drug, for example, has been injected through the cannula, the device for pulling out the cannula is restrained at the patient in order to retract the cannula into the device. The cannula is retracted into the device in order to hide the tip of the cannula and, by so doing, to decrease the risk of injury. The counter pressure, exerted on the device during this procedure, may cause the tip of the cannula to become slightly curved before it is pulled out, so that the closing element of the port is damaged by the deformed tip during the retraction. For example, small parts of the closing element could be cut out so that, after being punctured repeatedly, the closing element may start to leak.

SUMMARY OF THE INVENTION

It is therefore an object of the invention to create a device of the type mentioned above, which, after an implanted port is punctured, makes it possible to withdraw the cannula easily and with the least possible destruction.

This objective is accomplished by a device for administering a cannula, which has
a basic element, for example, for supporting the device on the skin of a patient,
a cannula, the tip of which, in the ready to use position of the device, protrudes beyond the basic element,
traction element, which is movable with respect to the basic element, and a separable prestressing device for prestressing the traction element with respect to the basic element in the ready to use position of the device,
wherein the traction element interacts with the cannula in such a manner that, when the prestressing device is released, the traction element retracts the tip of the cannula back into the basic element.

In the ready to use position, the traction element preferably is disposed at the basic element and, in particular, is held at the latter. Preferably, the traction element is disposed at a lid of the device.

Since, according to the invention, the prestressing device retracts the cannula by way of the traction element, the basic element can, in the meantime, be held fast in the unchanged position without the need for exerting a counter pressure in the direction of the puncture site. By these means, it is ensured that the tip of the cannula is not curved or bent. Accordingly, the cannula is taken care of and damage to the port is avoided. In addition, the inventive device may be operated with one hand, since a second hand is not required for taking hold of the cannula. This simplifies the progress of the work appreciably.

The device is used in that, in the ready to use position, the cannula, protruding with its tip over the basic element, is introduced through the skin of the patient into the port implanted thereunder. In so doing, the basic element of the device comes to rest against the skin of the patient and can then serve to support the device on the skin of the patient. After, for example, a medicament has been injected via the cannula, the basic element is held firmly, for example, by taking hold of it at the side, for pulling out the cannula, and the pretensioning device is separated. By these means, the tip of the cannula is retracted automatically into the basic element.

Advantageous developments of the invention arise out of the dependent claims.

Preferably, the device is designed for a one-handed manipulation for holding the basic element in place and for releasing the pretensioning device, while the basic element is in contact with the skin of a patient. This means that the needle can be pulled out while, at the same time, the basic element is held fast, and that only one hand is required for this. In contrast to this, a manipulation with two hands is always required for administering a cannula with conventional devices, since the cannula is pulled out with one hand in that, for example, a handle element is taken hold of and pulled away from a basic element in a direction parallel to the main axis of the cannula, while the device is restrained at the patient with a second hand.

Preferably, the device has at least one actuating element for releasing the prestressing device, the actuating device being actuated by moving, especially by pressing the actuating element in a direction at right angles to the cannula. Accordingly, for releasing the prestressing device, pressure is not exerted in the direction of the port. Preferably, especially the actuating element is actuated by pressing the actuating element in the direction of the central axis of the cannula. In particular, the aforementioned pressing is pressing with one hand, that is, with one or more fingers.

Preferably, the basic element can be held by taking hold of the actuating element and of an opposite side of the actuating element, especially with only one hand.

Preferably, the pretensioning device can be released by pressing the actuating element by taking hold of the basic element at the side. Preferably, the actuating element can be pressed in a direction at right angles to the cannula, in order to release the pretensioning device. In other words, the pretensioning device can be released in that the actuating element can be pressed in a direction at right angles to the cannula by laterally taking hold of the basic element at least in one area of the actuating element and exerting pressure on the actuating element.

Together with the cannula, inserted into the skin of the patient, the device is thus taken hold of at the side with one hand, that is, at right angles to the cannula on two opposite sides, for example, with two fingers, such as the forefinger and the thumb, and the pretensioning device is released by a compression.

Preferably, a locking element is disposed at the actuating element and a counter piece to the locking element, which is held in the ready to use position at the locking element, is disposed at the traction element. The pretensioning device is released in that the locking element releases the counter piece. For example, the locking element, disposed at the actuating element, is released from its counter piece by pressing and shifting the actuating element in the direction of the central axis of the cannula. It is particularly preferred if the actuating element forms the locking element or several locking elements for corresponding counter pieces of the traction element. Since there is only a movement at right angles to the direction of the cannula and accordingly at right angles to the direction of force of the pretensioning device, the pretensioning device can be released particularly easily, without the need for exerting a force in the direction of the port.

Preferably, the actuating element is plate-like and held at the basic element. In the ready to use position, the traction element is locked at the actuating element; the locking can be released by moving the actuating element in a direction at right angles to the cannula. As a result, the construction of the device is particularly simple and flat.

Preferably, the actuating element is held movably at the basic element and, in particular, displaceably in a direction at right angles to the cannula. In the ready to use position, at least one locking element of the traction element engages from behind a locking element of the actuation element in the form of a region of the actuating element. This region is shaped, so that it can be disengaged from the locking element of the traction element by moving the actuating element in a direction at right angles to the cannula. Since the region of the actuating element releases the locking element of the traction element in this manner, the pretensioning device is releaseable.

Preferably, a region, engaged from the rear in the ready to use position by a locking element of the traction element, is located at an edge of the actuating element, particularly at a lateral edge, which edge runs at right angles to a displacement direction of the actuating element and/or at which edge the actuating element is held displaceably at the basic element.

The arrangement of several such locking elements of the traction element in the ready to use position around the cannula, for example, four locking elements at opposite edges of an essentially rectangular actuating element, is particularly preferred. Preferably, a recess, through which the respective locking element can pass for its release, is provided at the respective region.

Since only a movement of the actuating element at right angles to the direction of the cannula and consequently at right angles to the direction of force of the pretensioning device is required for releasing the locking elements of the actuating element from the counter pieces of the traction element, the pretensioning device can be released particularly easily. Moreover, it is sufficient to provide a single, displaceable actuating element, which can be shifted, for example, directly by pressing against the outer edge thereof, which is disposed at the periphery of the device.

In a further embodiment, the at least one actuating element is disposed at a frame, which extends in the vicinity of the outer edge of the basic element and is connected at its ends with the basic element. In particular, the frame extends semi circularly around the basic element. By these means, the frame with the actuating element can be taken hold of particularly well. Furthermore, because it is connected with the basic element on both sides, the frame ensures that the actuating element is guided to some extent.

Optionally, two actuating elements for releasing the pretensioning device are disposed opposite to one another at the basic element. As a result, the actuating elements are particularly suitable for holding the basic element with one hand and, while simultaneously compressing the two actuating elements, a lateral displacement of the cannula or the exertion of a transverse force on the cannula is effectively prevented. The two frames of the fastening element form, for example, a ring, which encompasses the basic element.

Preferably the device has at least one closing element for hiding the tip of the cannula, when the latter is retracted into the basic element.

Optionally, the closing element can be moved by the force of a spring into a position, in which the tip is hidden. For example, the closing element may be disposed at a spring element and be pretensioned in the ready to use position and actuated by actuating the actuating element, in order to assume a hiding position, in which the tip is retracted into the basic element. For example, the closing element may be pretensioned laterally against the cannula in the ready to use position. When the tip of the cannula is retracted past the closing element into the basic element, the closing element is thus triggered automatically. The closing element may, for example, be a plate-like element, which is constructed in one piece with a laterally protruding leaf spring. By loosening the pretensioning, the plate-like element can be moved laterally and transversely to the cannula.

It is particularly preferred if the actuating element forms the closing element. Preferably, the actuating element has an opening for the cannula in the ready to use position. Since the actuating element forms the closing element directly, a construction results, which can be actuated a particularly easily and reliably.

Preferably, the closing element is disposed in the vicinity of an underside of the basic element, that is, in the vicinity of the side directed to the tip of the cannula. This is the side facing the skin of the patient. For example, the device has two closing elements on opposite sides, which can be shifted into a position, in which the front ends thereof are in front of the tip. Due to the at least one closing element, damage to the tip of the cannula after use of the device is precluded. Preferably, the closing element is held so that it can be shifted at the basic element.

Preferably, the closing element is held at the basic element so that, if the actuating element is pressed in the direction at right angles to the cannula, the closing element can be moved in front of the tip of the cannula, which has been retracted into the basic element. This is accomplished, for example, in that the actuating element has a finger or is connected with a finger or controls a finger, which shifts the closing element. For example, the finger may be disposed at the above mentioned locking element or connected therewith. By these means, the pretensioning device can be released with a single movement of the actuating element and, after the cannula has been retracted immediately, the closing element can be moved in front of the tip.

In turn, it is particularly preferred, if the actuating element forms the closing element.

Preferably, the device has a locking arrangement for locking the closing element in the position, in which the tip is hidden. The locking arrangement preferably consists of detent elements, which are provided at the actuation element and at the basic element. For example, the displaceable actuating element, held at the basic element, may have detent lugs, which protrude transversely to the displacement direction and engage the position in the detent notches of the basic element, hiding the tip. Furthermore, the locking arrangement may, for example, consist of a second locking element, which is connected with the actuating element or is disposed at this element and of a receptacle at the basic element assigned to the locking element. The locking element may be disposed, for example, at the aforementioned finger. The locking arrangement ensures that the tip of the cannula is not exposed once again.

The locking with the detent element prevents the closing element being pushed back once again.

Preferably, the actuating element is plate-like and is held displaceably at the basic element, forms the above-mentioned closing element and, in the ready to use position, engages the above-mentioned locking elements of the traction element. The pretensioning element can be released by shifting the actuating element and, by shifting the actuating element further, a closing region of the actuating element can be moved in front of the tip of the cannula, which has been retracted into the basic element. Since first of all the pretensioning device is released by pressing on the actuating element, so that the cannula can be retracted and the tip of the cannula is then hidden and optionally the actuating element is locked in the position hiding the tip, the pretensioning device is released and the retracted cannula is secured thereby by a single, linear movement of the actuating element. A particularly functionally secure construction of the device and very reliable handling accordingly thus result.

Optionally, the device has at least one latch, which protrudes into the basic element transversely to the cannula and can be advanced by actuating the actuating element. The latch has the locking element, forms a finger for moving the closing element in front of the tip of the cannula, which is retracted into the basic element, and has a component of the locking arrangement for locking the closing element. With this component, the latch can be engaged at the basic element at an assigned receptacle. Preferably, the latch is connected with the actuating element or is a part of the latter. The locking arrangement accordingly consists of its component, which forms a part of the latch, and of the assigned receptacle at the basic element. Preferably, the latch protrudes in the direction of the central axis of the cannula into the basic element. Since the latch is moved in this direction by pressing on the actuating element, first of all the pretensioning device is released by a single, linear movement, so that the cannula is retracted, and the closing element is then pushed in front of the tip of the cannula, the latch being engaged at the basic element. As a result, the closing element cannot be pushed back again. Once again, the handling of the device is very simple. This construction of the device is also particularly secure functionally.

Once again, by pressing on the actuating element with a single, linear movement, the pretensioning device is released, the closing element is shifted in front of the tip of the cannula and the latch is engaged at the basic element.

Preferably, the cannula is a port-puncturing needle for a port catheter system, in particular, a Huber needle. Preferably, the cannula is provided with a connection for a tube.

Preferably, in the vicinity of the tip, the cannula is provided with a section, the cross-section of which is enlarged relative to a cannula shaft. This is the case, for example, for a port needle, which has a Huber ground surface and a cannula shaft with a diameter of 1.1 mm and, at a bend in the vicinity of the tip, a maximum diameter of 1.4 mm. Preferably, at a site remote from the underside of the basic element, the latter has a passage opening for the shaft of the cannula and this passage opening has a cross-section, through which the section of the cannula with the enlarged cross-section cannot pass. In the example named, the passage opening is cylindrical with a diameter of 1.2 mm. The passage opening and the closing element or actuating element are disposed so that, when the tip of the cannula is retracted, the cannula section with the enlarged cross-section remains hanging at the passage opening, so that the tip of the cannula is in the interior of the basic element between the passage opening and the closing element. With that, secure protection against injury is achieved.

Preferably, the pretensioning device has a compression spring, which is disposed between the basic element and the traction element or a lid, at which the traction element is disposed. The compression spring is, for example, a helical spring, preferably a spirally extending, for example, conical leaf spring, the main loading direction of the compression spring extending in the direction of the cannula. Preferably, the compression spring is disposed ring-shaped or spiral-shaped around the middle axis of the cannula. Preferably, in the case of the pretensioned pretensioning device, the transverse extension of the compression spring is larger than the axial extension and, in particular, several times as large as the axial extension. This results in a flat construction of the device.

Preferably, a bottom element, particularly a bottom plate of the basic element, is disposed in front of an underside of the actuating element, that is, in front of that side, at which the cannula protrudes in the ready to use position. Preferably, this forms a support for supporting the device on the skin of the patient. The movement of the actuating element is facilitated by such a bottom element while the device is lying in contact with the skin of the patient, since the actuating element does not have to be shifted directly on the skin.

Preferably, in the longitudinal direction of the cannula, the actuating element is at a distance from the supporting surface of the basic element for supporting the device on the skin of a patient.

BRIEF DESCRIPTION OF THE DRAWINGS

In the following, examples of the invention are explained in greater detail by means of the drawing, in which.

DETAILED DESCRIPTION

Figure 1:
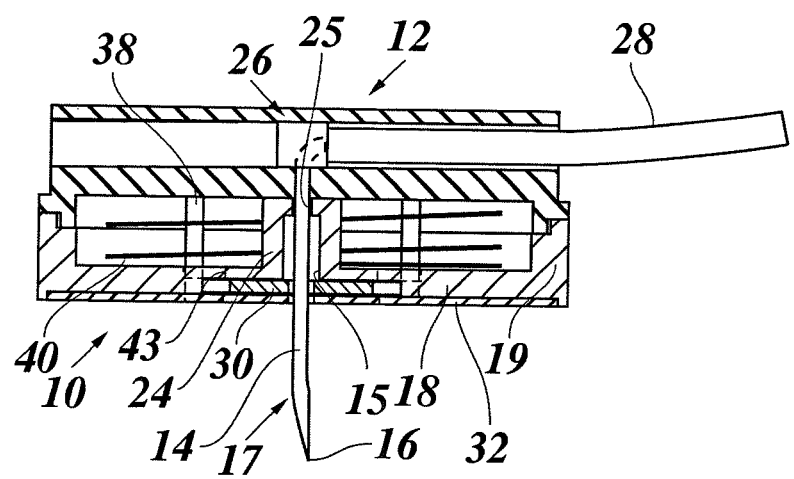
FIG. 1 shows a section through an inventive device with a basic element and a traction element in the form of a lid, at which the cannula is held.

The device, shown in FIG. 1, has a housing, which consists of a basic element 10 and a traction element 12, which, at the same time, forms a lid of the housing. The basic element 10 and the traction element 12 have essentially a cylindrical external cross section. Along their common central axis, a cannula 14 is disposed, the tip 16 of which protrudes through an opening 15 in the basic element 10 and, in the ready to use position shown in FIG. 1, protrudes so far beyond the flat underside of the basic element 10, that a port of a port catheter system, implanted subcutaneously, can be reached. The protruding length of the cannula is dimensioned, for example, so that, when the cannula 14 is introduced into the port, the basic element 10 can be supported with its underside on the skin of the patient. The cannula 14 is constructed, for example, as a Huber needle and has a shaft with a diameter of 1.1 mm and, above the cannula opening at a bend, a section 17 with a maximum diameter of 1.4 mm.

The basic element 10 forms a flat pot 18 with a ring-shaped side wall 19. In the center of the pot 18, an internal, cylindrical wall 24, which at its upper end has a passage opening for the shaft of the cannula in the form of a constriction 25 with a diameter of, for example, 1.2 mm, is formed above the opening 15.

The traction element 12 forms a lid for the pot 18 and, in the center thereof, carries a holding device 26 for the cannula 14 and a tube 28, which is connected liquid-tight therewith.

In a depression at the underside of the pot 18, a plate-shaped element 30 is mounted displaceably and is received at its underside by a bottom plate 32 of the basic element 10. In FIG. 1, the element 30 can be shifted back and forth in the viewing direction.

Figure 2:
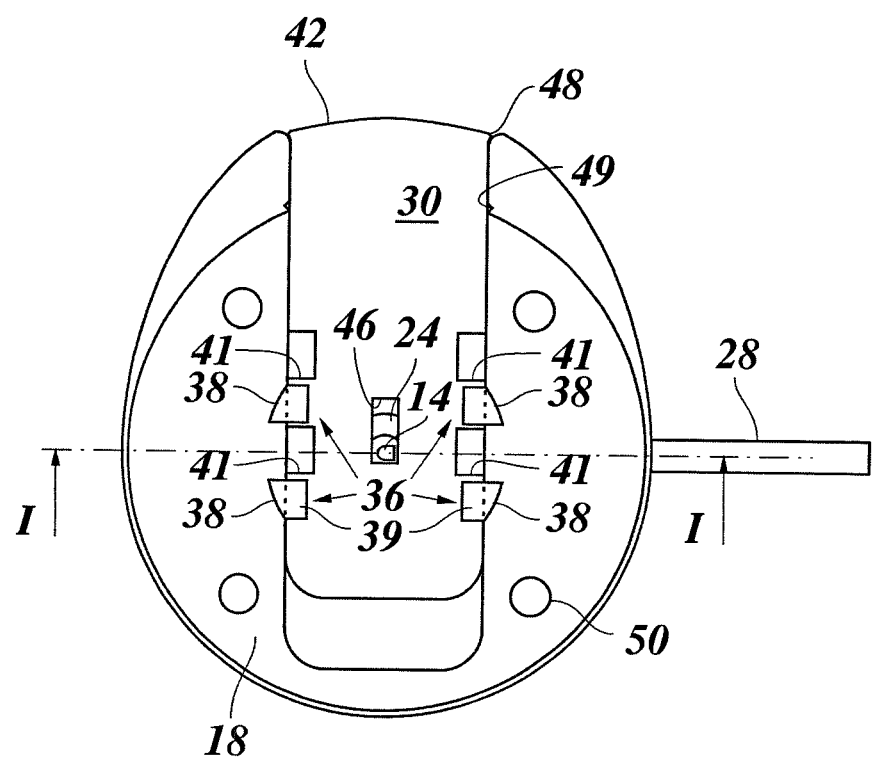
FIG. 2 shows a view of the device from below with the bottom plate removed, the line I-I corresponding to the section shown in FIG. 1.
Figure 3:
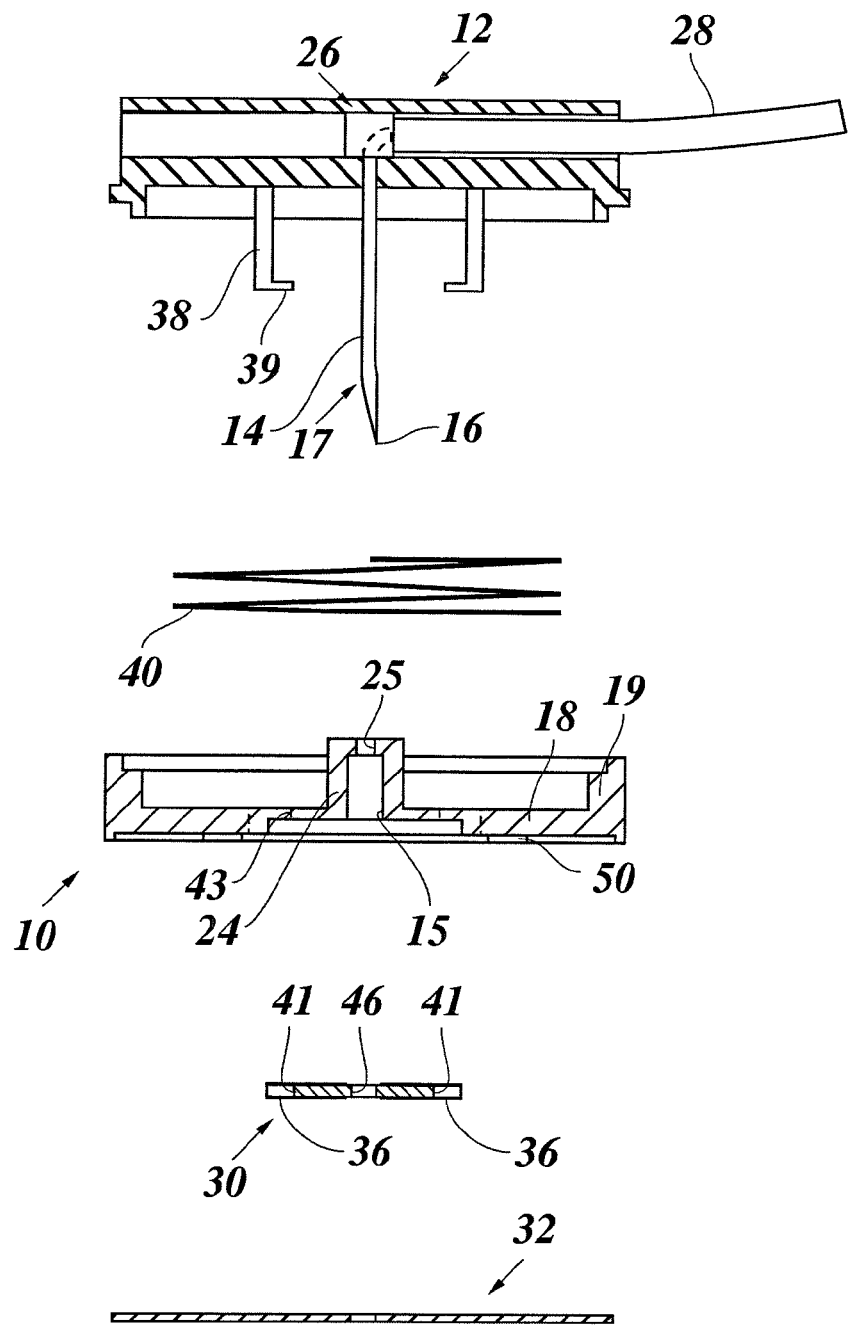
FIG. 3 shows an exploded representation of the device corresponding to FIG. 1.

FIG. 2 shows that the actuating element forms locking elements in the form of regions 36. Counter pieces 38 thereto are formed at the underside of the traction element 12 in the form of locking elements, which protrude downward from either side of the element 30 and are essentially L-shaped with a projection 39 extending below a region of the element 30. This can be seen especially in FIGS. 2 and 3. For a better illustration, FIG. 3 shows the sectional view of FIG. 1 in an exploded representation.

In a ready to use position of the device, element 30 is taken hold of from the rear at the regions 36 of the counter pieces 38 with the projections 39, so that the traction element 12 is locked by way of the projections 39 at the element 30 and, accordingly, at the basic element 10. In this position, the traction element 12 is pretensioned against the basic element 10, in that a compression spring 40 (FIG. 1) is disposed pretensioned between the bottom of the pot 18 and the lid of the traction element 12. FIG. 3 also shows the compression spring 40 in the pretensioned state.

In FIG. 2, it can be seen that the element 30 has the regions 36, as well as lateral recesses 41 at the edge. At its front edge (in FIG. 2 at the top), the element 30 has a gripping surface 42 which is freely open and accessible by a first finger of a hand of a person. The pretensioning device, formed by the locking elements 38, the regions 36 of the element 30 engaging the pretensioning device and the compression spring 40, is released by taking hold of the gripping surface 42 and pressing the element 30 inward in the direction of the central axis of the cannula 14, in that element 30 is shifted, so that the projections 39 reach the recesses 41 and are released by the regions 36. Appropriate recesses 43 are provided in the bottom of the pot 18 and indicated by broken lines in FIG. 1.

Because of the release of the locking elements 38, the traction element 12 is lifted from the basic element 10 by the pressure of the compression spring 40. At the same time, the projections 39 emerge upward out of the bottom of the pot 18. The gripping surface 42 and the element 30 accordingly form an actuating element for releasing the pretensioning device.

When the traction element 12 is lifted from the basic element 10, it takes along the cannula 14. By these means, the tip 16 is retracted behind the opening 15. Element 30 has a sufficiently large opening 46, to permit element 30 to be shifted in spite of the cannula 14 passing through. The cannula, with its section 17 of larger cross section, gets stuck at the constriction 25 of the wall 24, so that the tip 16 is hidden in the interior of the pot 18, surrounded by the wall 24 and, in this way, protected against contact.

When element 30 is pushed further, it finally closes the opening 15 in that a closed region of the element 30 is now located in front of the tip 16 of the cannula 14, which has been retracted into the basic element 10. Small detent lugs 48, which, when element 30 is pushed in completely, engage detent accommodations 49 in the bottom of the pot 18, are formed laterally at the element 30. The detent lugs 48 and the detent accommodations 49 together form a locking device for the element 30, which prevents element 30 being pushed back. By these means, the opening 15 is closed reliably, so that the tip 16 of the cannula 14 cannot emerge once again. Accordingly, the element 30 hides the tip 16.

By taking hold of the gripping surface 42 and, optionally, the opposite side of the pot 18 of the device described and pressing the element 30 inward, initially the locking element 38 of the lid of the traction element 12 is released through the recesses 41 and, in this way, the pretensioning device is released and the cannula 14 is retracted into the basic element 10. As the element 30 is pressed in further, it ends up in front of the retracted tip 16 of the cannula 14, hiding the latter, and is locked in this position by the locking device 48, 49.

Figure 4:
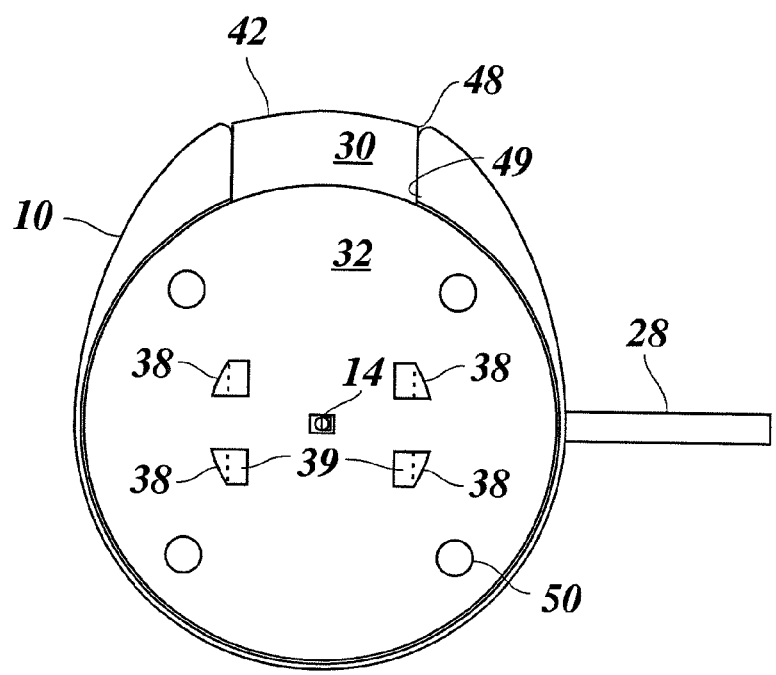
FIG. 4 shows a view of the device, together with the bottom plate, from below.

FIG. 4 shows a view corresponding to FIG. 2, however, with the bottom plate 32 set down. The latter is aligned over four projections 50 at the underside of the pot 18 and corresponding recesses in the bottom plate 32. The bottom plate 32 also has recesses for the locking elements 38 with the projections 39, so that a particularly flat construction is achieved.

Figure 5:
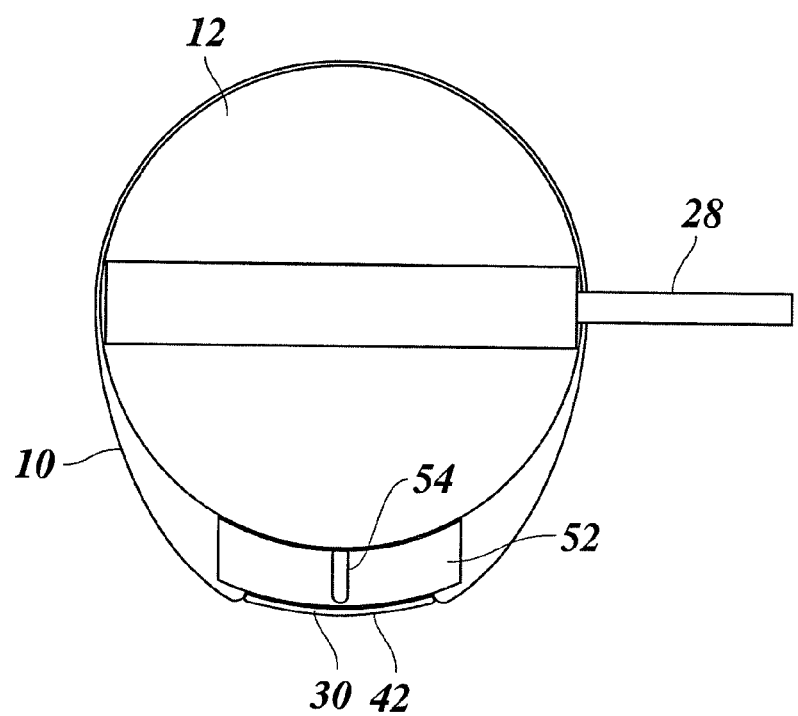
FIG. 5 shows a view of the device from above.

FIG. 5 shows a view of the device from above. A safety element 52 is inserted between an upwardly protruding edge of the element 30, at which the gripping surface 42 is formed, and the outer wall of the pot 18. The safety element 52 may be jammed, for example, between an upwardly protruding edge of the element 30 and the wall of the pot 18. Its function is to prevent element 30 being pushed in accidentally. The safety element 52 can be removed by taking hold of a handle 54, when the device is to be actuated.

Figure 6:
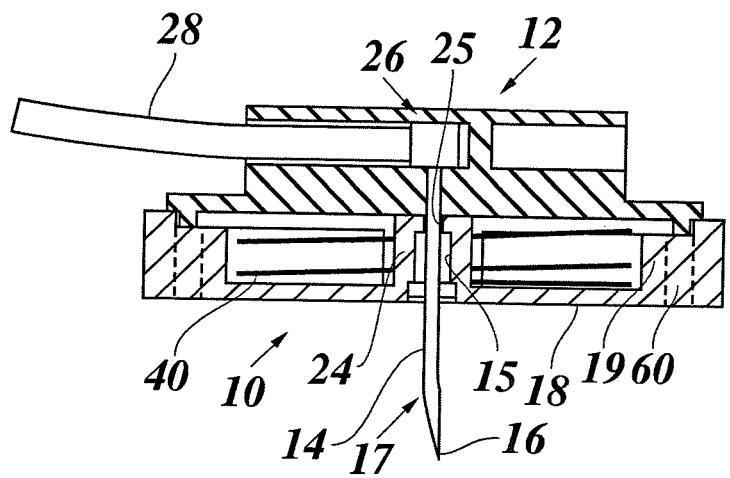
FIG. 6 shows a section through a device of a second embodiment with a basic element and a traction element in the form of a lid, at which a cannula is held.
Figure 7:
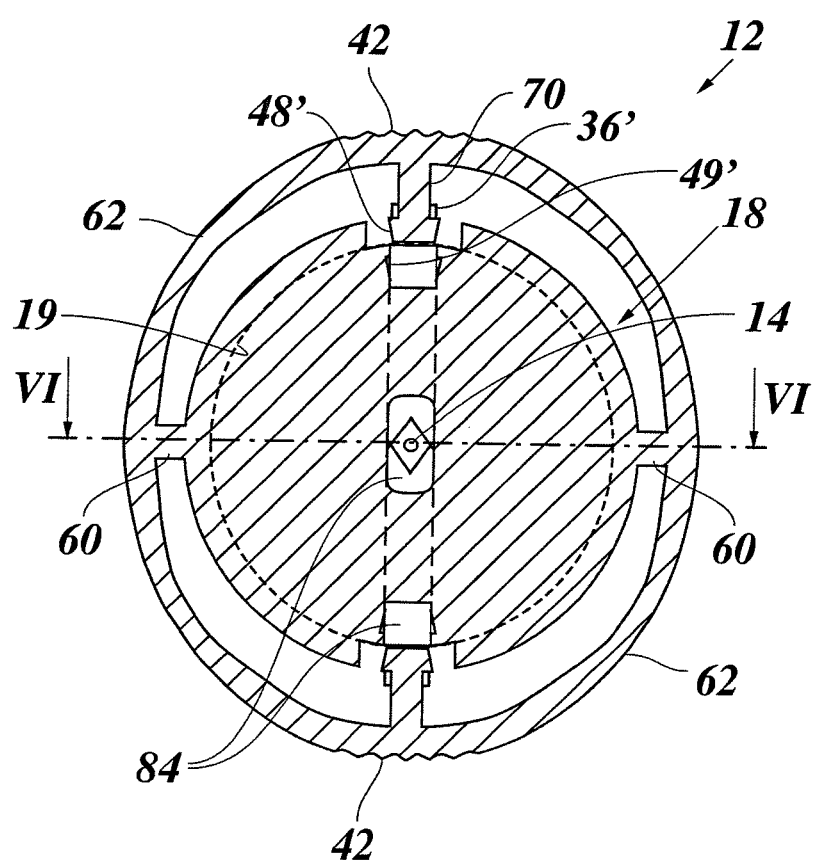
FIG. 7 shows a view of the basic element of the device of FIG. 6 from below, the line VI-VI corresponding to the section shown in FIG. 6
Figure 8:
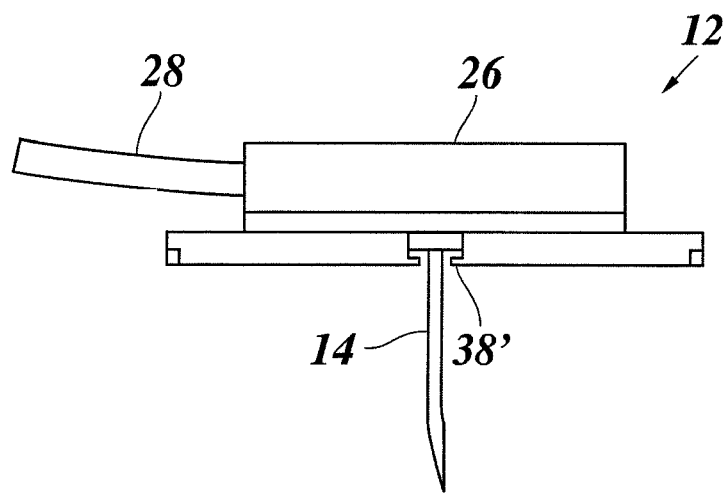
FIG. 8 shows a side view of the traction element and the lid of FIG. 6 with the cannula.

FIGS. 6 to 8 show a second embodiment of the device, which differs from that shown in FIGS. 1 to 5 with respect to the number and type of actuating elements as well as the construction of the locking device for the pretensioning device. Elements, which correspond to one another, have been given the same reference numbers.

The side wall 19 of the pot 18, indicated by a broken line in FIGS. 6 and 7, and the pot 18 are surrounded at a distance by an annular element, which is connected with the pot 18 at two opposite sides by bridges 60 and, in this way, is divided into two frames 62 in the form of half rings.

FIG. 7 shows that, at each frame 62, a latch 70, directed inwardly to the pot 18, is integrally molded in the middle between the bridges 60. At its front end, the latch 70 forms a harpoon-like spread 48', which interacts with a suitably shaped detent receptacle 49'. When the latch 70 is pushed into the detent receptacle 49', the spread 48' engages the detent receptacle 49', so that the latch 70 is held firmly.

Locking elements 36' are formed on the latches 70 in the shape of lateral projections behind the spread 48'. These locking elements 36' are disposed at the upper side of the latch 70. Corresponding locking elements, which form counter pieces 38' of the locking elements 36' and, in the ready to use position, are held at the locking elements 36', so that the traction element 12 is locked at the latches 70 and, with that, at the basic element 10, are disposed at the edge of the lid of the traction element 12. In this position, the traction element 12 is pretensioned in turn against the basic element 10, in that the compression spring 40 (FIG. 6) is disposed pretensioned between the bottom of the pot 18 and the lid of the traction element 12.

At the outside in each case opposite the latch 70, the frames 62 have a gripping surface 42. The pretensioning device, formed by the locking elements 36', the counter pieces 38' thereof and the compression spring 40, is released by taking hold of the opposite gripping surfaces 42 and pressing the latches 70 inward in the direction of the central axis of the cannula 14, in that the locking elements 36' are moved radially inward and, at the same time, release the counter pieces 38', so that the traction element 12 is raised up from the basic element 10 by the pressure of the compression spring 40. The gripping surfaces 42 and the latch 70 accordingly form the actuating element for releasing the pretensioning device. In much the same way as with the first embodiment, the cannula 14 is taken along when the traction element 12 is raised from the basic element 10 and the tip, surrounded by the wall 24, is hidden in the interior of the pot 18.

Two mutually opposite closing elements, in the form of closing plates 84, are disposed displaceably in the bottom of the pot 18. The closing plates 84 are on an imaginary line, connecting the two latches 70 and passing through the cannula 14, and can be shifted parallel to this line. The closing plates 84 extend to the outside in each case as far as just before the latch 70, so that, when the latch 70 is pushed into the detent receptacle 49', they are advanced in the direction of the center axis of the cannula 14. When the latch 70 with the spread 48' is locked at the detent receptacle 49', the respective front end of the closing plate 84 is in front of the tip 16 of the cannula 14, which has been retracted into the basic element 10. Accordingly, the latch 70 forms a finger for moving the closing plate 84 inward from the tip 16 of the retracted cannula 14. The spread 48' and the detent receptacle 49' together form a locking device for the closing plate 84, which prevents the closing plate 84 being pushed back. By these means, the opening 15 is closed reliably, so that the tip 16 of the cannula 14 cannot emerge once again. Accordingly, the closing plates 84 hide the tip 16.

For the second embodiment of the device, by taking hold of the gripping surfaces 42 which are freely open and accessible by the fingers of a hand of a person and pressing the frames 62 together, it is achieved, first of all, that the locking elements 36' release the lid of the traction element 12 by pressing the latches 70 inward and thus release the pretensioning device, and that the cannula 14 is retracted into the basic element 10, whereupon, as the latches 70 are pressed inward further, the closing plates 84 move in front of the tip 16 of the cannula 14, hiding the latter, and are locked in this position by the locking device 48', 49'.

The invention claimed is:

1. A device for administering a cannula comprising:
   a basic element having a structure such that a tip of the cannula protrudes beyond the basic element in a ready to use position of the device,
   a traction element which is movable with respect to the basic element,
   a releasable pretensioning device for pretensioning the traction element with respect to the basic element in the ready to use position of the device,
   at least one actuating element formed on the basic element for releasing the pretensioning device, the at least one actuating element movable in a direction at a right angle to the cannula, wherein the at least one actuating element comprises a first gripping surface that is arranged at a side of the basic element, the at least one actuating element adapted to be actuated by pressing at least the first gripping surface of the at least one actuating element in the direction at the right angle to the cannula towards a central axis of the cannula, and the traction element being separate from and movable away from the at least one actuating element,
   the at least one actuating element including a first actuating element movable in the direction at the right angle to the cannula towards the central axis of the cannula and having said first gripping surface which is freely open and accessible by a first finger of a hand of a person,
   one of:
      a portion of the basic element directly opposite to the first gripping surface of the first actuating element, and
      a second gripping surface of a second actuating element of the at least one actuating element arranged at another side of the basic element directly opposite to the first gripping surface of said first actuating element and movable in a direction at a right angle to the cannula towards the central axis of the cannula, wherein the traction element is separate from and movable away from the second actuating element, being freely open and accessible for engagement by a different finger of said hand of the person simultaneously with engagement of the first gripping surface of the first actuating element by the first finger of the person,
   at least one closing element mounted to the basic element for hiding the tip of the cannula, when the tip has been retracted into the basic element,
   wherein the at least one closing element is held at the basic element in such a way, that the at least one closing element is movable relative to the basic element such that the at least one closing element is moved relative to the basic element to a position in front of the tip of the cannula, and such that the tip of the cannula is hidden in the basic element, by pressing said at least one actuating element in the direction at the right angle to the cannula towards the central axis of the cannula, wherein a movement of the at least one actuating element in the direction towards the central axis of the cannula causes movement of the at least one closing element to said position in front of the tip of the cannula that has been retracted into the basic element,
   wherein the traction element interacts with the cannula so that, when the pretensioning device is released, the tip of the cannula retracts into the basic element, and
   wherein the device is designed for a one-handed operation for holding the basic element and releasing the pretensioning device, while the basic element is resting on skin of a patient.

2. The device of claim 1, wherein the pretensioning device includes:
   a locking element disposed at the at least one actuating element, and
   a counter piece to the locking element in the ready to use position, disposed at the traction element, and
   the pretensioning device is released when the locking element releases the counter piece.

3. The device of claim 1, wherein the at least one actuating element is plate-like and held at the basic element and the traction element is locked at the at least one actuating element in the ready to use position, wherein locking of the basic element and the traction element is adapted to be released by moving the at least one actuating element in the direction at the right angle to the cannula.

4. The device of claim 1, wherein the at least one actuating element is held movably at the basic element in the direction at the right angle to the cannula and, in the ready to use position, at least one counter piece of the traction element engages from a rear a locking element of the at least one actuating element in a region of the at least one actuating element, the region being shaped so that said region is disengaged from the at least one counter piece of the traction element by moving the at least one actuating element in the direction at the right angle to the cannula.

5. The device of claim 1, further comprising a locking device for locking the at least one closing element in a position hiding the tip.

6. The device of claim 1, wherein, in a vicinity of the tip, the cannula has a section with a cross-section, which is larger than a cross-section of a main shaft of the cannula, both cross-sections taken in a direction at right angles to a lengthwise direction of the cannula at a respective point of said respective cross-section and wherein the basic element, at a place remote from an underside of the basic element, at which underside the cannula, in the ready to use position, protrudes with the tip, has a passage opening, for said main shaft of the cannula, and the passage opening has a cross-section, through which the section of the cannula with the larger cross-section cannot pass.

7. The device of claim 1, wherein the cannula is a port puncture needle for a port catheter system.

8. The device of claim 1, wherein said releasable pretensioning device is movable only in an axial direction of the cannula when released by the at least one actuating element, such that the cannula is also only movable in the axial direction thereof.

9. The device of claim 1,
wherein the basic element has a form of a flat pot with a ring-shaped side wall,
wherein the basic element has a flat underside and is adapted to support the device with the flat underside on the skin of the patient, and
wherein, in the ready to use position, the cannula protrudes with the tip from the underside of the basic element.

10. The device of claim 1, wherein the at least one actuating element forms the at least one closing element.

11. The device of claim 1, wherein the device comprises a finger, which is at least one of:
a part of the at least one actuating element, and
connected with the at least one actuating element, and controlled by the at least one actuating element,
wherein the at least one actuating element is adapted for moving the at least one closing element in front of the tip of the cannula by means of the finger shifting the at least one closing element.

12. The device of claim 1, wherein the basic element has a form of a flat pot with a ring-shaped side wall, wherein the basic element further has an inner wall which, at an upper end thereof, comprises a passage opening for a main shaft of the cannula.

13. A device for administering a cannula comprising:
a basic element having a structure such that a tip of the cannula protrudes beyond the basic element in a ready to use position of the device,
a traction element which is movable with respect to the basic element, and
a releasable pretensioning device for pretensioning the traction element with respect to the basic element in the ready to use position of the device,
at least one actuating element formed on the basic element for releasing the pretensioning device, the at least one actuating element movable in a direction at a right angle to the cannula, wherein the at least one actuating element comprises a first gripping surface that is arranged at a side of the basic element, the at least one actuating element adapted to be actuated by pressing at least the first gripping surface of the at least one actuating element in the direction at the right angle to the cannula towards a central axis of the cannula, and the traction element being separate from and movable away from the at least one actuating element,
the at least one actuating element including a first actuating element movable in the direction at the right angle to the cannula towards the central axis of the cannula and having said first gripping surface which is open and accessible by a first finger of a hand of a person,
one of:
a portion of the basic element directly opposite to the first gripping surface of the first actuating element, and
a second gripping surface of a second actuating element of the at least one actuating element arranged at another side of the basic element directly opposite to the first gripping surface of said first actuating element and movable in a direction at a right angle to the cannula towards the central axis of the cannula, wherein the traction element is separate from and movable away from the second actuating element, being freely open and accessible for engagement by a different finger of said hand of the person simultaneously with engagement of the first gripping surface of the first actuating element by the first finger of the person,
at least one closing element mounted to the basic element for hiding the tip of the cannula, when the tip has been retracted into the basic element,
wherein the traction element interacts with the cannula so that, when the pretensioning device is released, the tip of the cannula retracts into the basic element, and
wherein, in a vicinity of the tip, the cannula has a section with a cross-section, which is larger than a cross-section of a main shaft of the cannula, both cross-sections taken in a direction at right angles to a lengthwise direction of the cannula at a respective point of said respective cross-section and wherein the basic element, at a place remote from an underside of the basic element, at which underside the cannula, in the ready to use position, protrudes with the tip, has a passage opening, for said main shaft of the cannula and the passage opening has a cross-section, through which the section of the cannula with the larger cross-section cannot pass,
wherein the device is designed for a one-handed operation for holding the basic element and releasing the pretensioning device, while the basic element is resting on skin of a patient.

14. The device of claim 13, wherein the basic element has a form of a flat pot with a ring-shaped side wall, wherein the basic element further has an inner wall which, at an upper end thereof, comprises said passage opening for the main shaft of the cannula.

\* \* \* \* \*